(12) United States Patent  (10) Patent No.: US 7,421,369 B2
Clarkson  (45) Date of Patent: Sep. 2, 2008

(54) ACTIVITY RECOGNITION APPARATUS, METHOD AND PROGRAM

(75) Inventor: Brian Clarkson, Tokyo (JP)

(73) Assignee: Sony Corporation, Tokyo (JP)

( * ) Notice: Subject to any disclaimer, the term of this patent is extended or adjusted under 35 U.S.C. 154(b) by 58 days.

(21) Appl. No.: 11/435,746

(22) Filed: May 18, 2006

(65) Prior Publication Data

US 2006/0284979 A1    Dec. 21, 2006

(30) Foreign Application Priority Data

Jun. 9, 2005    (JP)    ............................. 2005-169507

(51) Int. Cl.
 G06F 19/00    (2006.01)
 G06F 17/40    (2006.01)
(52) U.S. Cl. ...................... 702/150; 73/379.01; 73/760; 73/763; 73/767; 73/774; 73/865.1; 73/865.4; 482/1; 482/8; 702/108; 702/113; 702/151; 702/152; 702/153; 702/189
(58) Field of Classification Search .............. 73/379.01, 73/432.1, 760, 763, 767, 774, 787, 865.1, 73/865.4; 482/1, 8; 702/1, 33, 34, 108, 113, 702/127, 150, 151, 152, 153, 182, 189
See application file for complete search history.

(56) References Cited

U.S. PATENT DOCUMENTS 3,304,787 A * 2/1967 Takewo et al. ............ 73/514.33
3,330,945 A * 7/1967 Gevas ............................ 701/4
3,428,789 A * 2/1969 Richard ....................... 702/153
3,559,492 A * 2/1971 Erdley ....................... 73/504.03
3,744,322 A * 7/1973 Pacey et al. ............... 73/504.04
3,899,028 A * 8/1975 Morris et al. ................. 172/4.5
3,974,699 A * 8/1976 Morris et al. ............... 73/865.9
4,821,572 A * 4/1989 Hulsing, II ............... 73/504.04
4,896,268 A * 1/1990 MacGugan ................. 701/220

(Continued)

FOREIGN PATENT DOCUMENTS

EP    1 066 793 A2 *    1/2001

OTHER PUBLICATIONS

Brian Clarkson, et al., "Recognizing User Context via Wearable Sensors", In Fourth International Symposium on Wearable Computers (ISWC), 2000, pp. 69-75.

(Continued)

*Primary Examiner*—Edward R Cosimano
(74) *Attorney, Agent, or Firm*—Oblon, Spivak, McClelland, Maier & Neustadt, P.C.

(57) ABSTRACT

There is provided an activity recognition apparatus for detecting an activity of a subject. The apparatus includes: a sensor unit including a plurality of linear motion sensors configured to detect linear motions and a plurality of rotational motion sensors, the linear motions being orthogonal to each other, the rotational motions being orthogonal to each other; and a computational unit configured to receive and process signals from the sensors included in the sensor unit so as to detect an activity of the subject. The sensor unit is directly or indirectly supported by the subject with an arbitrary orientation with respect to the subject. The computational unit performs a calculation that uses the signals from both linear motion sensors and rotational motion sensors to determine the activity of the subject independent of the orientation of the sensor unit.

9 Claims, 6 Drawing Sheets

U.S. PATENT DOCUMENTS

| | | | | |
|---|---|---|---|---|
| 5,128,671 | A | * | 7/1992 | Thomas, Jr. .................. 341/20 |
| 5,178,012 | A | * | 1/1993 | Culp ........................... 73/510 |
| 5,297,028 | A | | 3/1994 | Ishikawa |
| 5,485,402 | A | | 1/1996 | Smith et al. |
| 5,583,776 | A | | 12/1996 | Levi et al. |
| 5,806,365 | A | * | 9/1998 | Zunino et al. ............ 73/514.16 |
| 5,955,667 | A | * | 9/1999 | Fyfe ............................ 73/490 |
| 6,018,998 | A | * | 2/2000 | Zunino et al. ............ 73/514.16 |
| 6,122,960 | A | | 9/2000 | Hutchings et al. |
| 6,176,837 | B1 | * | 1/2001 | Foxlin ........................ 600/595 |
| 6,301,964 | B1 | * | 10/2001 | Fyfe et al. .................... 73/510 |
| 6,409,687 | B1 | * | 6/2002 | Foxlin ........................ 600/595 |
| 6,513,381 | B2 | * | 2/2003 | Fyfe et al. .................... 73/510 |
| 6,522,266 | B1 | | 2/2003 | Soehren et al. |
| 6,834,436 | B2 | * | 12/2004 | Townsend et al. ............. 33/512 |
| 6,853,909 | B2 | | 2/2005 | Scherzinger |
| 2002/0040601 | A1 | * | 4/2002 | Fyfe et al. .................... 73/490 |
| 2002/0170193 | A1 | | 11/2002 | Townsend et al. |
| 2003/0045816 | A1 | * | 3/2003 | Foxlin ........................ 600/595 |
| 2004/0143176 | A1 | * | 7/2004 | Foxlin ........................ 600/395 |
| 2005/0033200 | A1 | * | 2/2005 | Soehren et al. ............. 600/595 |
| 2006/0284979 | A1 | * | 12/2006 | Clarkson .................... 348/143 |

OTHER PUBLICATIONS

Holger Junker, et al., "Continuous Recognition of Arm Activities With Body-Worn Inertial Sensors", In Proceedings of the 8th International Symposium on Wearable Computers, 2004, pp. 188-189.

Paul Lukowicz, et al., "Recognizing Workshop Activity Using Body Worn Microphones and Accelerometers", In Second IEEE International Conference on Pervasive Computing and Communications, 2004, pp. 18-32.

Thomas P. Minka, "Old and New Matrix Algebra Useful for Statistics", Technical report, Massachusetts Institute of Technology, 2000, pp. 1-19.

Mathias Staeger, et al., "Implementation and Evaluation of a Low-Power Sound-Based User Activity Recognition System", In Eighth International Symposium on Wearable Computers (ISWC), 2004, pp. 138-141.

Thad Starner, et al., "Real-Time American Sign Language Recognition Using Desk and Wearable Computer Based Video", IEEE Transactions on Pattern Analysis and Machine Intelligence, vol. 20, No. 12, Dec. 1998, pp. 1371-1375.

Tero Tolonen, et al., "A Computationally Efficient Multipitch Analysis Model", IEEE Transactions on Speech and Audio Processing, vol. 8, No. 6, Nov. 2000, pp. 708-716.

* cited by examiner

ACTIVITY RECOGNITION APPARATUS, METHOD AND PROGRAM

BACKGROUND OF THE INVENTION

1. Field of the Invention

The present invention relates to an apparatus, method, program and storage medium for activity recognition. More specifically, the present invention relates to an activity recognition apparatus, an activity recognition method, a program to cause a computer to perform such a method, a storage medium or memory storing such a program, and a signal coded to cause a computer to perform such a method.

2. Description of Related Art

Human activity classification has been attempted with cameras, microphones (Non-patent Document 5), inertial sensors (Non-patent Document 4), and goniometers. For each sensor or combination of sensors, researchers have also developed custom algorithms that to varying degrees can classify activity. Since one part of human activity classification is obtaining accurate measurements of human motion, the technology used overlaps with methods used for character animation, kinesiology and biomechanics. However, since the inventor of the present application are addressing the problem of how to determine and classify human activities in a mobile and unconstrained context, all except a few sensor modalities are appropriate.

Computer Vision

One set of such constrained methods involves monitoring the subject with static cameras or wearable cameras (Non-patent Document 10). Often optical markers are attached to the subject's body to simplify visual tracking. The subject's movement can be inferred from the movement of the markers through an inverse-kinematic model.

While this method has the potential of providing very rich and complete measurements, it can only be used in the well-lit space in view of the cameras, which precludes its use in mobile applications.

Computer Audition

There also examples where researchers have tried using microphones (both on the body and in the environment) to automatically determine a user's activity (see Non-patent Document 2 and Non-patent Document 9). However, major advantages of motion sensors are lower data rate (which translates to much lower computational requirements) and the ability to measure only the motion of the user. In audio, sounds caused by the user's activities are mixed with an ever-changing background of environmental sounds. Separation of these foreground and background is an unsolved problem which does not arise when using motion sensors.

Absolute Joint Angle Sensing

This set of methods involves attaching sensors directly to the subject's body so as to measure the angles of the subject's joint. Possible sensor's are potentiometers and rotational encoders (which both require an exoskeleton to transmit the changes in a subject's joint angles to the sensor), bend sensors (strips of material that are sensitive to bending and flexing), and inertial sensors (accelerometers and gyros, which essentially measure changes in velocity via Newton's First Law of Motion). In clinical situations, goniometers (equivalent to a tilt sensor) are often used to measure angles with respect to gravity.

Inertial Sensing

Of all these only the inertial sensors and tilt sensors can be used to measurement of a subject's movements without requiring extensive modifications to clothing (for exoskeletons or strips of flex-sensitive material) or requiring special attachments. Furthermore, inertial sensors can be completely enclosed inside another device that user can simply hold or carry in a pocket or bag, thus making these sensors attractive for use in mobile devices or as self-contained devices.

Other relevant works are disclosed, for example, in Non-patent Document 7, Non-patent Document 8, Patent Document 1, Patent Document 2.

REFERENCES

Non-Patent Document 1: Dimitri P. Bertsekas. Nonlinear Programming. Athena Scientific, 2nd edition, 1995.

Non-Patent Document 2: Brian Clarkson, Alex Pentland, and Kenji Mase. Recognizing user context via wearable sensors. In Fourth International Symposium on Wearable Computers (ISWC), 2000.

Non-Patent Document 3: Masataka Ishikawa. U.S. Pat. No. 5,297,028: Method and apparatus for correcting drift errors in an angular rate sensor. Filed by Zexel Corporation Daihatsu-Nissan, Tokyo, Japan, August 1991.

Non-Patent Document 4: Holger Junker, Jamie Ward, Paul Lukowicz, and Gerhard Troster. Continuous recognition of arm activities with body-worn inertial sensors. In Proceedings of the 8th International Symposium on Wearable Computers, 2004.

Non-Patent Document 5: Paul Lukowicz, Jamie Ward, Holger Junker, Mathias Stager, Gerhard Troster, Amin Atrash, and Thad Starner. Recognizing workshop activity using body-worn microphones and accelerometers. In Second IEEE International Conference on Pervasive Computing and Communications, 2004.

Non-Patent Document 6: Thomas P. Minka. Old and new matrix algebra useful for statistics. Technical report, Massachusetts Institute of Technology, 2000.

Non-Patent Document 7: Bruno Scherzinger. U.S. Pat. No. 6,853,909: Walking stick navigator for position determination. Filed by Applanix Corporation, Inc., Ontario, Canada, November 2002.

Non-Patent Document 8: Douglas Smith, Aaron Joseph, David Boone, Robert Borchers, and Ernest Burgess. U.S. Pat. No. 5,485,402: Gait activity monitor. Filed by Prosthetics Research Study, Seattle, Wash., March 1994.

Non-Patent Document 9: Mathias Staeger, Paul Lukowicz, and Gerhard Troester. Implementation and evaluation of a low-power sound-based user activity recognition system. In Eighth International Symposium on Wearable Computers (ISWC), 2004.

Non-Patent Document 10: Thad Starner, Josh Weaver, and Alex Pentland. Real-time american sign language recognition using desk and wearable computer-based video. IEEE Transactions on Pattern Analysis and Machine Intelligence, 20(12):1371-175, December 1998.

Non-Patent Document 11: Tero Tolonen and Matti Kaijalainen. A computationally efficient multipitch analysis model. IEEE Transactions on Speech and Audio Processing, 8(6), November 2000.

Patent Document 1: Robert Levi and Thomas Judd. U.S. Pat. No. 5,583,776: Dead reckoning navigational system using accelerometer to measure foot impacts. Filed by Point Research Corporation, Santa Ana, Calif., March 1995.

Patent Document 2: Christopher Townsend and Steven Arms. U.S. Pat. No. 6,834,436: Posture and body movement system. Filed by MicroStrain, Inc., Williston, Vt., February 2002.

SUMMARY OF THE INVENTION

However, obtaining accurate motion measurements with inertial sensors has historically proven to be quite difficult due to the sensitivity these sensors have to shock, temperature, electrical noise and so on. For example, gyros (angular rate sensors) have a dependency on temperature which must be accounted for Non-patent Document 3.

Calibration is also required since these devices will typically have an arbitrary offset and scale factor affecting their outputs.

Further, inertial sensors have no notion of the subject's frame of reference and measurements are always relative to the physical sensor. One exception to this, is that a properly oriented accelerometer can measure the earth's gravitational field and thus providing a way to determine the down direction. The accelerometer must not be undergoing any other unknown accelerations for this to work.

Accordingly, in view of the above-mentioned issues, it is desirable to perform activity recognition using inertial sensors without posing any preconditions on orientation of the inertial sensors relative to the subject's reference frame, thereby allowing more flexibility in implementing a system for the activity recognition.

According to an embodiment of the present invention, there is provided an activity recognition apparatus for determining an activity of a subject. The activity recognition apparatus includes: a sensor unit including a plurality of linear motion sensors configured to detect linear motions and a plurality of rotational motion sensors, the linear motions being orthogonal to each other, the rotational motions being orthogonal to each other; and a computational unit configured to receive and process signals from the sensors included in the sensor unit so as to determine an activity of the subject. The sensor unit is directly or indirectly supported by the subject with an arbitrary orientation with respect to the subject; and the computational unit performs processing that uses the signals from both linear motion sensors and rotational motion sensors to determine the activity independent of the orientation of the sensor unit.

According to another embodiment of the present invention, there is provided an activity recognition method of determining an activity of a subject. The method includes: sampling accelerations in three orthogonal axes and angular velocities around the three orthogonal axes; and determining an activity of the subject using all the sampled accelerations and angular velocities. In the method, the accelerations and angular velocities are detected by sensors integrated into a single unit, which is directly or indirectly supported by the subject with an arbitrary orientation with respect to the subject; and the determination of activity is performed by using both the accelerations and angular velocities to determine the activity independent of the orientation of the sensor unit.

According to another embodiment of the present invention, there is provided a program that causes a computer to perform activity recognition by determining an activity of a subject, or a recoding medium that store such a program, or a signal coded to cause a computer to perform such a program. The program includes: receiving data of accelerations in three orthogonal axes and angular velocities around the three orthogonal axes; and determining an activity of the subject using all the received data of accelerations and angular velocities. The accelerations and angular velocities are detected by sensors integrated into a single unit, which is directly or indirectly supported by the subject with an arbitrary orientation with respect to the subject; and the determination of activity is performed by using both the accelerations and angular velocities to determine the activity independent of the orientation of the sensor unit.

In the embodiments of the present invention, the sensor unit is directly or indirectly supported by the subject with arbitrary orientation. In other words, the signals from the sensor unit do not have any information about the sensor's orientation with respect to the coordinates of the subject. However, different movements of the entire sensor unit correspond with different activities of the subject.

Accordingly, the activity of the subject can be determined independent of the sensor unit's orientation by detecting the movement of the entire sensor unit and by associating the detected movement with a corresponding activity of the subject or a corresponding motion signature that associated with the activity.

According to the present invention, it is possible to perform activity recognition using inertial sensors without posing any preconditions on orientation of inertial sensors relative to the subject's reference frame, thereby allowing more flexibility in implementing a system for the activity recognition.

BRIEF DESCRIPTION OF THE DRAWINGS

The above and other objects, features and advantages of the present invention will become more apparent from the following description of the presently preferred exemplary embodiments of the invention taken in conjunction with the accompanying drawings, in which.

DETAILED DESCRIPTION OF THE EMBODIMENTS

Embodiments of the present invention are described with reference to accompanying figures.

Figure 1:
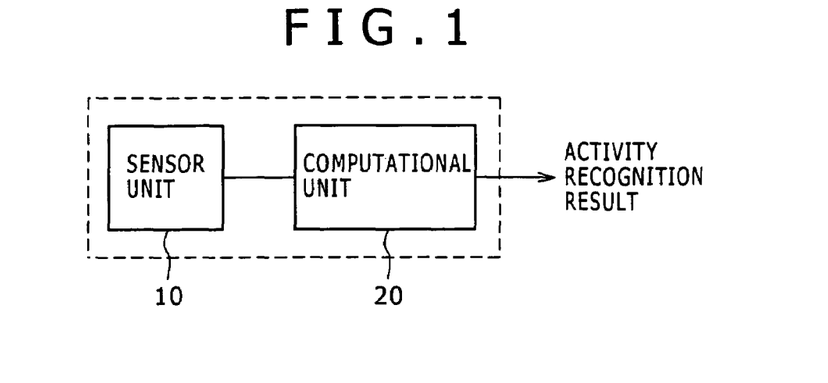
FIG. 1 is a block diagram of an activity recognition apparatus according to an embodiment of the present invention.

FIG. 1 shows a configuration example of an activity recognition apparatus for determining an activity of a subject in accordance with an embodiment of the present invention. The apparatus includes a sensor unit 10 and a computational unit 20. The sensor unit 10 includes a plurality of linear motion sensors configured to detect linear motions and a plurality of rotational motion sensors, the linear motions being orthogonal to each other, the rotational motions being orthogonal to each other. The computational unit 20 is configured to receive and process signals from the sensors included in the sensor unit so as to output an activity of the subject. The sensor unit 10 is directly or indirectly supported by the subject with an arbitrary orientation with respect to the subject. The computational unit 20 performs a calculation that uses the signals from both linear motion sensors and rotational motion sensors to determine the activity independent of the orientation of the sensor unit.

The plurality of linear motion sensors may be three accelerometers for measuring accelerations in three orthogonal axes, and the plurality of rotational motion sensors may be three gyro sensors for measuring angular velocities around the three orthogonal axes. The computational unit 20 may use six outputs from the accelerometers and the gyro sensors to determine a current activity of the subject.

The computational unit may includes; a buffer configured to store an observation sequence formed of a plurality set of the sensor outputs for a predetermined period of time; a storage configured to store a plurality of reference sequences, the reference sequences corresponding to motion signatures of different activities; and a matching processor configured to match the observation sequence against the reference sequences to find a best matched reference sequence. Further, the matching processor may find an optimal rotation and temporal correspondence between the observation sequence and one of the reference sequences so as to obtain the best matched reference sequence.

Furthermore, the reference sequence may include a plurality of vectors representing states in Hidden Markov Model; and the matching between the observation sequence and the reference sequence may be performed using Viterbi algorithm so as to obtain an optimal state path.

Alternatively, the computational unit may further detect a rate of the subject's gait by calculating an autocorrelation of the signals from the linear motion sensors and an autocorrelation of the signals from the rotation motion sensors, and summing these autocorrelations to obtain a summary autocorrelation function; and the summary autocorrelation function may be used to determine the rate of the subject's gait.

Alternatively, the computational unit may further detect a rotation of the sensor unit by calculating a first rotation by integrating the signals from the rotational motion sensors, calculating a second rotation by using a gravitation model and the signals from the linear motion sensors, and performing weighted interpolation of the first and second rotation. Further, the weight for the first rotation is larger if variations in the signals from the rotational motion sensors are smaller; and the weight for the second rotation is larger if variations in the signals from the linear motion sensors are smaller.

Alternatively, the activity recognition apparatus may further include a storage configure to store reference motion signatures and corresponding locations for a reference activity. Furthermore, the computational unit may further detect a location of the sensor unit on the subject by determining if a current activity represented with the signals from the sensors is the reference activity, and, if the current activity is the reference activity, matching a motion signature corresponding to the current activity against the reference motion signature so as to determine a location of the sensor unit, which corresponds to a best matched reference motion signature.

According to another embodiment of the present invention, there is provided an activity recognition method of determining an activity of a subject. The method includes: sampling accelerations in three orthogonal axes and angular velocities around the three orthogonal axes; and determining an activity of the subject using all the sampled accelerations and angular velocities. Furthermore, the accelerations and angular velocities are detected by sensors integrated into a single unit, which is directly or indirectly supported by the subject with an arbitrary orientation with respect to the subject; and the determination of activity is performed by using both the accelerations and angular velocities to determine the activity independent of the orientation of the sensor unit.

According to another embodiment of the present invention, there is provided a program that causes a computer to perform activity recognition by determining an activity of a subject. The program includes: receiving data of accelerations in three orthogonal axes and angular velocities around the three orthogonal axes; and determining an activity of the subject using all the received data of accelerations and angular velocities. Furthermore, the accelerations and angular velocities are detected by sensors integrated into a single unit, which is directly or indirectly supported by the subject with an arbitrary orientation with respect to the subject; and the determination of activity is performed by using both the accelerations and angular velocities to determine the activity independent of the orientation of the sensor unit.

Below, still another embodiment according to the present invention is described. In the following embodiment, there is provided a system that is capable of activity recognition and includes a sensor unit and a computational unit. In the following embodiment, it is assumed that the sensor unit is "supported" by a human subject and the computational unit determines a type of current activity of the human subject based on the outputs from the sensor unit.

(1) System Overview

Figure 2:
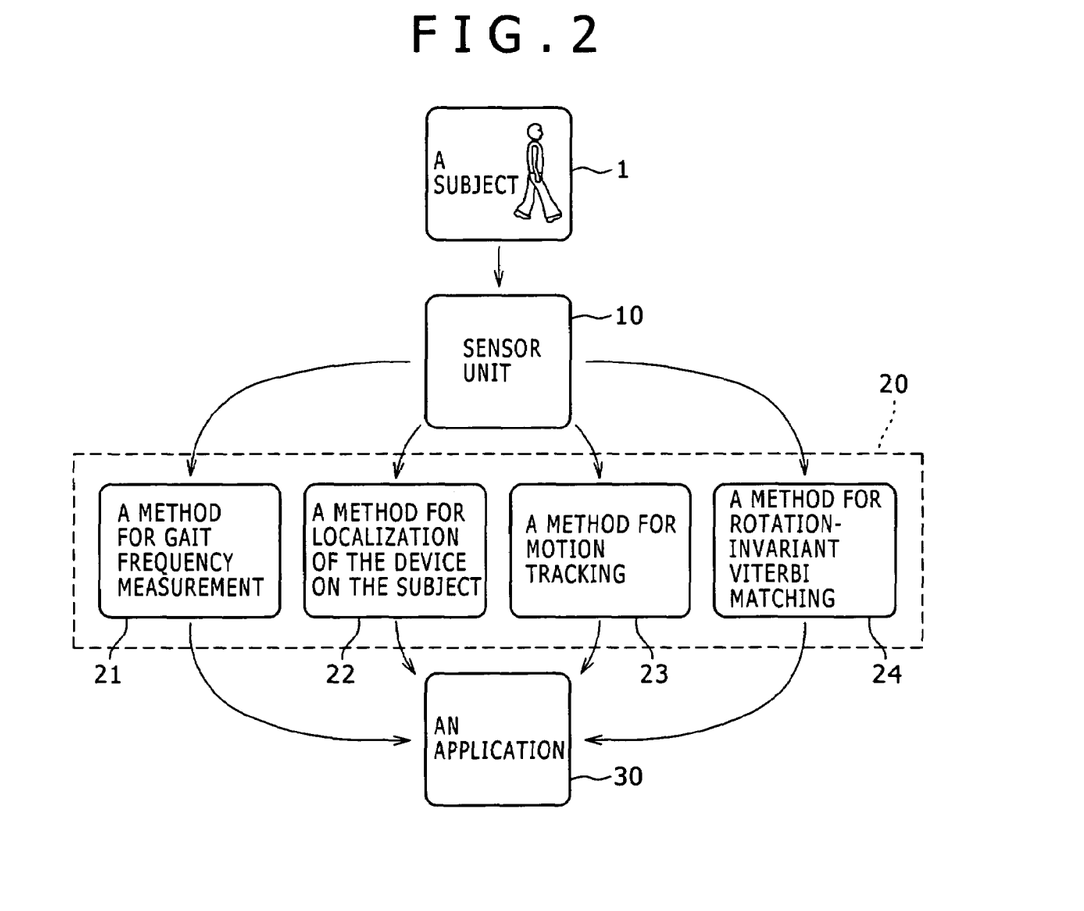
FIG. 2 is an conceptual overview of an activity recognition apparatus according to an embodiment of the present invention.

In the present embodiment, as shown in FIG. 2, a six degree-of-freedom (DOF) inertial sensor is employed as the sensor unit 10 to classify various common human activities in real-time. In the following description, the term "the Sensor" indicates the 6-DOF inertial sensor, and "the User" denotes the human subject 1 who is either carrying or wearing the Sensor. Furthermore, the term "the Device" denotes the present system combining an inertial measurement unit (IMU) with the Sensor and the above-mentioned computational unit 20 for performing steps of methods for classification of the User's activity. Results of classification may be outputted or transfer to an application 30.

While using inertial sensors to measure human activity has been attempted before, the present system defining characteristic is its ability to operate fully automatically almost anywhere on the human body with any sensor orientation. In the present embodiment, the system incorporates four distinct methods for different aspects of the User's activity and device state, each of which can be performed without posing any preconditions on the sensor orientation. The methods includes a method 21 for gait frequency measurement, a method 22 for localization of the Device on the User, a method 23 for motion tracking, and a method 24 for rotation-invariant Viterbi matching (see FIG. 2).

The Sensor may be supported or held by the User directly or indirectly. For example, the following (nonexhaustive) manner of coupling may be possible:

The User is holding the Sensor in his hands.

The User is carrying the Sensor in a purse or backpack which is being worn.

The Sensor is rigidly or semi-rigidly attached to the User's body or clothing.

The Sensor is hanging from the User's neck or waist.

The Sensor has been integrated into the construction of the User's shoes, jewelry, hat, gloves, portable electronic device or any other object whose normal use involves being worn or carried by the User.

The Sensor is attached or place inside a vehicle that is simultaneously transporting the User.

The present embodiment may also be applicable even in cases where the Sensor is coupled to the User with any arbitrary forms as long as the Sensor's motions have a relationship with the User's motions.

(2) Physical Device

For the purposes of a simple and concrete description of the present embodiment, it is assumed that the 6-DOF inertial sensor is composed of components that measure linear acceleration in the x-, y-, and z-directions and angular velocity around the x-, y-, and z-axis. However, the methods described hereafter can be trivially adapted to other schema for measuring 6-DOF.

Figure 3A:
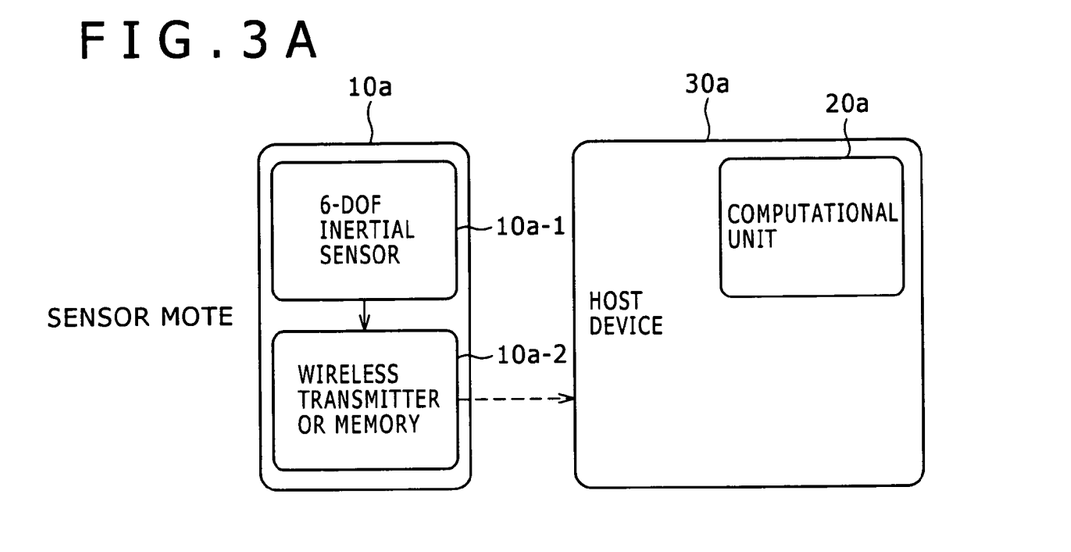
FIGS. 3(a) and 3(b) are schematic diagrams of activity recognition apparatuses for different usage scenarios.

In the present embodiment, as shown in FIG. 3(a), the system may include a sensor mote 10a and a computational unit 20a embedded in a host device 30a. The sensor mote 10a includes a 6-DOF inertial sensor 10a-1 and a wireless transmitter 10a-2 for transmitting sensor data to the computational unit 20a. Alternatively, a memory may be provided instead of the wireless transmitter 10a-2 for storing sensor data for a certain period of time. The stored data may be transferred to the computational unit 20a when the sensor mote 10a is connected to the host device 30a.

Figure 3B:
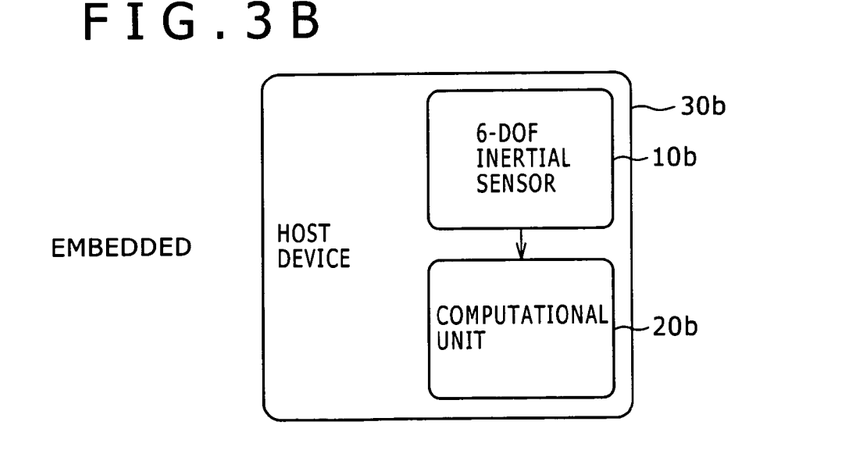

Alternatively, the entire system including a 6-DOF inertial sensor 10b and a computational unit 20b may be embedded in a single host device 30b such as a cellphone or portable game apparatus as shown in FIG. 3(b).

(3) Sensor Signal Conditioning and Calibration

Below, there is described the computational processing of the raw sensor data from the Sensor so as to yield classifications of the User's activities in real-time. First, some symbols representing the raw output of the Sensor are defined:

$$u(t) = \begin{bmatrix} s_i(t) \\ s_j(t) \\ s_k(t) \end{bmatrix} \in R^3 \quad (1)$$

$$v(t) = \begin{bmatrix} s_\theta(t) \\ s_\phi(t) \\ s_\psi(t) \end{bmatrix} \in R^3 \quad (2)$$

Figure 4:
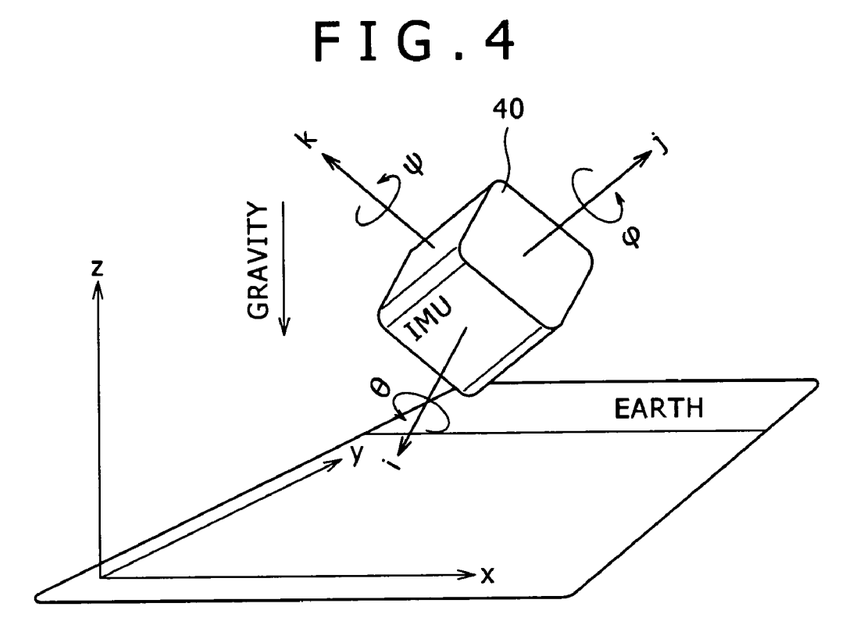
FIG. 4 is an conceptual overview of a physical module (IMU) according to an embodiment of the present invention.

Each sample from the Device's sensors contains the six values specified in Equations (1) and (2). The u(t) sensor values are linearly proportional to the acceleration of the Device along the i-, j-, and k-axes. These could be considered to be measured, for example, by MEMS accelerometer or similar devices. The v(t) sensor values are linearly proportional to the angular velocity of the Device around the i-, j-, and k-axes. These 10 could be considered to be obtained, for example, from MEMS gyros or similar devices. FIG. 4 shows all the measurements are made with respect to basis directions in the local coordinate system (i-j-k) of the Device itself.

If it is supposed that $p(t) \in R^3$ is the position of the Device in any world coordinate system (e.g. x-y-z in FIG. 4), $g(t) \in R^3$ is the acceleration of the Earth's gravitational field in the local coordinate system, and $q(t) \in R^3$ is the orientation of the Device in its local coordinate system, then it can be written:

$$u(t) = A[\nabla^2 p(t) + g(t)] + u_0 + \epsilon_u(t) \quad (3)$$

$$v(t) = B\nabla q(t) + v_0 + \epsilon_v(t) \quad (4)$$

All gradients are taken with respect to the local coordinate system of the Device. A and B are 3-by-3 scaling matrices. The diagonal elements specify the scale-factors (also known as sensitivities) which convert the sensor output (e.g. a voltage) to standard physical units (e.g. m/s² and °/s). At the same time, the off-diagonal elements describe the cross-talk between sensors due to slight misalignments (for example, the angle between the θ and φ gyros is not exactly 90°). The arbitrary offsets (also known as bias) exhibited by typical sensors are denoted by $u_0$ and $v_0$. The sensor noise, which includes the quantization noise, is specified for each sensor as a sequence of random variables, $\epsilon_u(t)$ and $\epsilon_v(t)$.

Equation (3) and (4) describe how the actual motion of the Device translates into sensor measurements. If it is solved for acceleration and angular velocity using the expressions in (3) and (4), then the following expressions are obtained:

$$\nabla^2 p(t) = A^{-1}[u(t) - u_0 - \epsilon_u(t)] - g(t) \quad (5)$$

$$\nabla q(t) = B^{-1}[v(t) - v_0 - \epsilon_v(t)] \quad (6)$$

Signal calibration involves determining the values of A, $u_0$, B, $v_0$. Depending on the actual components used inside the IMU, these values can be dependent on manufacturing conditions, ambient temperature, driving voltage, and so on. However, only the method for motion tracking require these parameters to be known. All of the other methods 21-22 and 24 given here can use uncalibrated sensor values.

Finally, either the continuous signals from the IMU are sampled at a given rate and passed onto the computational unit or the signals leave the IMU already digitized. For the remainder of this description, let $r_{imu}$ be the digital sampling rate of the output of the IMU. Thus the digitized output of the IMU can be written as:

$$u[t] = u(t/r_{IMU}) \quad (7)$$

$$v[t] = v(t/r_{IMU}) \quad (8)$$

$$t = 0, 1, 2, \ldots \quad (9)$$

(4) Method for Gait Frequency Measurement

This Section describes our method for determining the User's activity, such as determining if the User is walking or running or not moving, and tracking the rate of his/her gait. This method is effective for any location of the device on the User's body. This method for gait detection and tracking involves tracking the period of repetitive movements apparent in the output of the acceleration sensors.

A common method for detecting and measuring the periods of periodic signals is by finding peaks in the autocorrelation of the signal. To see how the autocorrelation of the acceleration sensor output, u, relates to the autocorrelation of the actual acceleration of the IMU, $\nabla^2 p$, (multivariate) autocorrelation of the i-th frame may be written as:

$$u \star u = \sum_{i=0}^{N_{gait}} u[i] \cdot u[i+t] \quad (10)$$
$$= \phi_1 + \phi_2 + \phi_3$$

where * denotes the cross-correlation operator and, $$\phi_1 = (A\nabla^2 p * A\nabla^2 p) + (Ag * Ag)$$

$$\phi_2 = 2(A\nabla^2 p * Ag)$$

$$\phi_3 = 2(A\nabla^2 p * \epsilon_u + A\nabla^2 p * u_0) + 2(u_0 * \epsilon_u) + (u_0 * u_0) + (\epsilon_u * \epsilon_u)$$

The first term of Equation (10), $\phi_1$, is the most important term containing the periodicities of the acceleration of the IMU and gravity (which depends only on the orientation of the IMU). The second term, $\phi_2$, is a cross-correlation between acceleration and gravity. For any kind of natural repetitive motion involving the human body, it is pretty much guaranteed that g(t) and $\nabla^2 p$ will share the same periodicities and hence their autocorrelations, $\phi_1$, and cross-correlations, $\phi_2$, will add constructively. The final term, $\phi_3$, contains correlations of the noise and the offset with various terms. These correlations will not exhibit any periodicities and will simply add noise and a constant bias to the final autocorrelation of Equation (10). The validity of the autocorrelation of the gyro sensor outputs, v, follows exactly the same argument.

In practice, a small time interval is chosen over which to conduct the autocorrelation analysis and a rate is chosen at which to perform the analysis. Let $T_{gait}$ be the length of time for one gait analysis frame (e.g. interval of sensor data) and let $r_{gait}$ be the rate of gait analysis. Thus, in Equation (10), $$N_{gait} = \lceil T_{gait} r_{IMU} \rceil \quad (11)$$

is the number of vectors in one analysis frame.

The present method involves calculating the autocorrelation of u and v and summing the result to get a summary autocorrelation function (SACF) of the total motion of the IMU:

$$\rho[t] = (u*u)[t] + (v*v)[t] \quad (12)$$

For efficiency and improvement of temporal resolution, the Wiener-Khinchin Theorem is used to calculate a windowed autocorrelation. In general, if x[t] is any sequence, $X[\omega] = F\{x\}$ is its Discrete Fourier Transform (DFT), and $W[\omega] = F\{w\}$ is the DFT of a windowing function (such as a Hamming window), then:

$$x*x = F\{|W*X|^2\} \quad (13)$$

Using the Fast Fourier Transform (FFT) to calculate the DFT in Equation (13) results in a very efficient calculation of the autocorrelations in Equation (12).

The peaks of the ACF correspond to the periods of any cyclic motion in the data. However, since the ACF will also contain peaks at integer multiples of the true period of any cycles, a peak pruning procedure similar to that introduced in Non-patent Document 11 is used to calculate an enhanced summary autocorrelation function (ESACF). This peak pruning technique is as follows:

PRUNE-HARMONICS(SACF) returns ESACF
1. Clip the SACF to positive values.
2. Upsample and interpolate by a factor of two.
3. Subtract the upsampled version from the clipped original.
4. Clip to positive values again.
5. Repeat 2-4 for prime factors three, five, seven, etc.

The goal of this procedure is to sequentially remove all multiples of each peak, thus leaving only the fundamental periods.

Now if the highest peak (for non-zero lags) and threshold are chosen, it is possible to determine when there is cyclic motion (such as walking) and at what pitch it is occurring at. If $\tau^*$ is the lag of the highest peak in the ESACF, then the pitch of the gait is:

$$P_{gait} = \frac{r_{IMU}}{\tau^*} \quad (14)$$

If there is no peak with a value over a certain threshold (defined as a percentage of the energy in the signal during the analysis interval), then the system can generate a report that the User is not walking or running (gait pitch=0 Hz). Since, the gait pitch changes over time, the above analysis is done repeatedly for each successive analysis interval, yielding gait pitch estimates at the rate of $r_{gait}$.

(5) Method for Motion Tracking

In this Section, the method 23 for tracking the down direction and heading continuously no matter how the orientation of the device changes or moves is provided. This method assumes that the output from the IMU has been calibrated.

The 3-axis of gyro sensing data contains enough information to track the IMU's orientation. However, all gyros suffer from an accumulation of drift and other types of error. Thus, using just gyro information to track orientation, while quite accurate in the short-term, leads to large tracking errors in the long term.

The 3-axis of acceleration sensing data contains information about what direction Earth's gravity is pulling. Knowledge of the direction of the Earth's gravitational pull can be used to track the IMU's orientation drift-free with at most two degrees of freedom. The problem with just using the accelerometers in this fashion is that when the IMU is being acted on (moved by some outside force) the estimate of the Earth's gravitational pull is corrupted.

It is very difficult and unnatural for humans to move or move another object with constant acceleration or velocity. Similarly, with respect to rotation, it is very difficult for humans to rotate or rotate another object with constant angular velocity.

In order to robustly estimate the down direction, it is preferable to rely on the acceleration measurements more when the accelerometer signal is constant because it is highly likely that a human is not acting on the device. Conversely, it is preferable to rely more on the gyro measurements when the accelerometer signal is non-constant.

This principle also applies to online re-zeroing of the gyro signal. In other words, it is preferable that Gyro measurements is re-zeroed when the gyro measurement is constant. Luckily, this is also true when relying mostly on the acceleration measurements for tracking.

Figure 6:
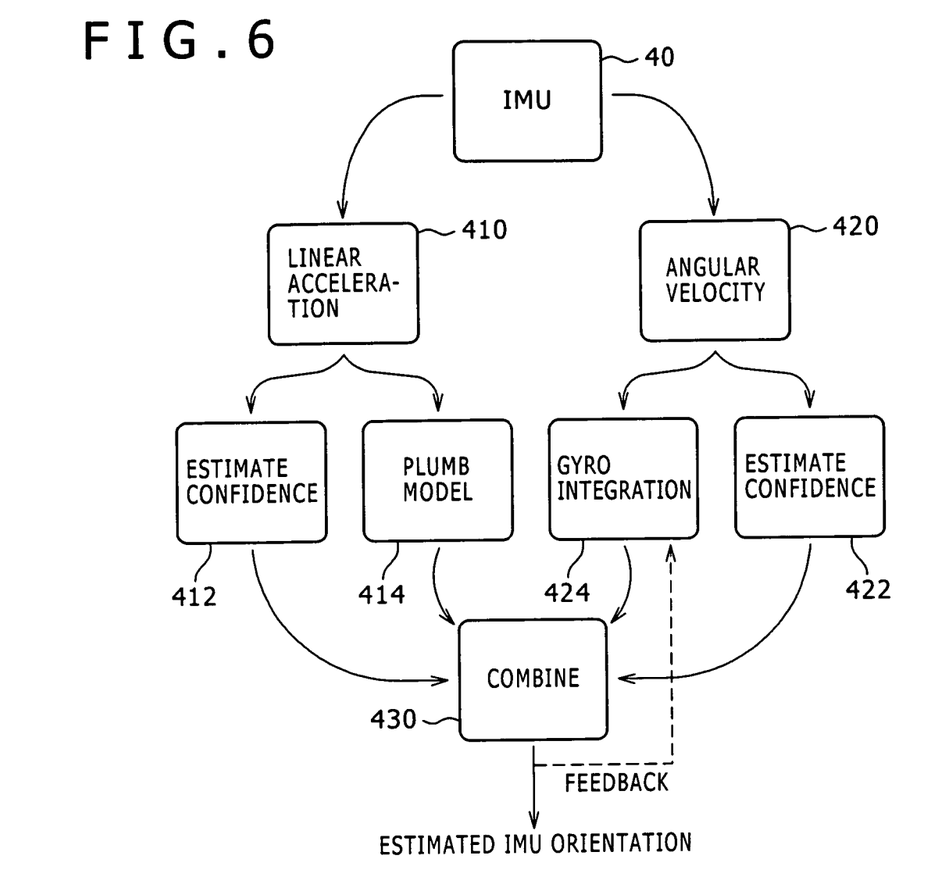
FIG. 6 is an overview of processing pipeline for a method of tracking an IMU's motion.

FIG. 6 shows the computational pipeline for the motion tracking method. Linear acceleration data 410 from the IMU 40 including the sensor is used to calculate the confidence 412 that only gravity is acting on the IMU 40 and as input into the Plumb Model 414 (explained later). Angular velocity data 420 from the IMU 40 is used to calculate the confidence 422 that the IMU 40 is not being rotated and as input into the Gyro Integration module 424.

Both the Plumb Model 414 and the Gyro Integration 424 output separate estimates of the IMU's orientation, i.e. $Q_{plumb}$ and $Q_{gyro}$ (described later). $Q_{plumb}$ and $Q_{gyro}$, are then combined using the confidence scores to weight one versus the other (430) to perform weighted interpolation to calculate the estimated IMU orientation. The Gyro Integration computes an orientation relative to the orientation of the previous timestep and thus requires feedback.

The Plumb Model 414 gives an absolute estimate of orientation and thus requires no feedback.

(5.1) The Plumb Model

The Plumb Model uses the Earth's gravitational pull to measure orientation, albeit only with two degrees of freedom. In short, this module outputs the rotation that maps the current down vector to a unit reference vector, r, in the coordinate system of the IMU 40 (see FIG. 4). This reference vector can be chosen arbitrarily, or during zeroing. The resulting rotation is given in quaternion form as:

$$Q_{plumb}[t] = \begin{bmatrix} a_x[t]\sin(\theta[t]/2) \\ a_y[t]\sin(\theta[t]/2) \\ a_z[t]\sin(\theta[t]/2) \\ \cos(\theta[t]/2) \end{bmatrix} \quad (15)$$

where $a[t]=(a_x[t], a_y[t], a_z[t])^T$ is the axis of rotation and $\theta[t]$ is the angle of rotation. The down vector is just the normalized linear acceleration (assuming no forces other than gravity are acting on the IMU 40):

$$d[t] = \frac{u[t]}{\sqrt{u[t]^T u[t]}} \quad (16)$$

The cross product of the reference vector and the down vector gives the axis of rotation:

$$a[t]=d[t] \times r \quad (17)$$

Figure 7:
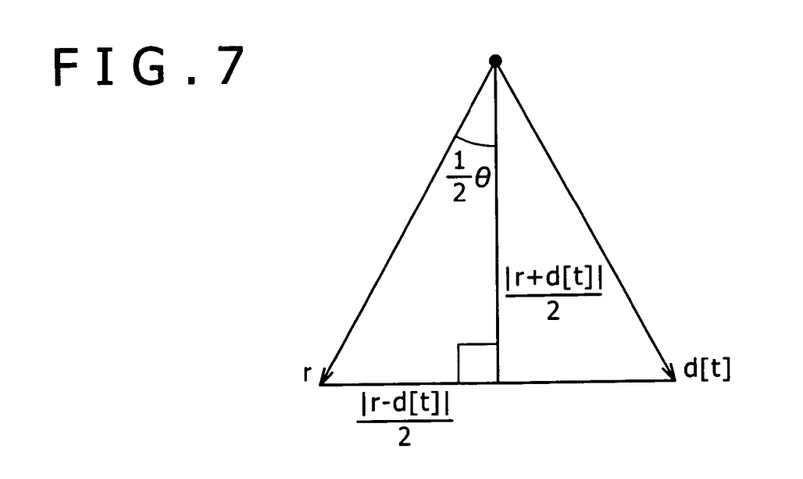
FIG. 7 is a schematic diagram showing a geometric construction used to directly calculate sine and cosine of a half-angles required by quaternion representation in a Plumb model.

The $\sin(\theta[t]/2)$ and $\cos(\theta[t]/2)$ are calculated directly (without using inverse trigonometric functions which are hard to implement in embedded applications) from FIG. 7 as:

$$\sin(\theta[t]/2) = \frac{|r+d[t]|}{2} \quad (18)$$

$$\cos(\theta[t]/2) = \frac{|r-d[t]|}{2} \quad (19)$$

(5.2) Gyro Integration

Integration of the gyro's angular velocity measurements is straightforward. As input, the previous orientation of the IMU, Q[t−1] is required. First, each axial rotation is represented as a quaternion rotation in local coordinates (i-j-k in FIG. 4):

$$q_i=(\cos(s_\theta[t]/2), (1, 0, 0)^T \sin(s_\theta[t]/2)) \quad (20)$$

$$q_j=(\cos(s_\phi[t]/2), (0, 1, 0)^T \sin(s_\phi[t]/2)) \quad (21)$$

$$q_k=(\cos(s_\Phi[t]/2), (0, 0, 1)^T \sin(s_\Phi[t]/2)) \quad (22)$$

Then these local quaternions are rotated into the world coordinate system using the previous orientation, Q[t−1], of the IMU:

$$Q_i=(\cos(s_\theta[t]/2), Q[t-1](1, 0, 0)^T Q[t-1]^{-1}\sin(s_\theta[t]/2)) \quad (23)$$

$$Q_j=(\cos(s_\phi[t]/2), Q[t-1](0, 1, 0)^T Q[t-1]^{-1}\sin(s_\phi[t]/2)) \quad (24)$$

$$Q_k=(\cos(s_\Phi[t]/2), Q[t-1](0, 0, 1)^T Q[t-1]^{-1}\sin(s_\Phi[t]/2)) \quad (25)$$

and combine them together into one quaternion representing the next orientation.

$$Q_{gyro}[t]=Q_i Q_j Q_k \quad (26)$$

(6) Method for Comparing Motion Signatures

The method 24 (see FIG. 2) presented in this Section solves the problem of how to compare unsynchronized motion signatures that are collected using IMU's with unknown orientations. For example, a typical application would require matching a realtime signal to a database of motion signatures. However, the orientation of the IMU might be arbitrarily different from the orientation of the IMU used to generate the motion signatures in the database. Furthermore, the proper way to temporally align a test signal to the motion signatures in the database must be determined.

A rotation-invariant Viterbi algorithm (RIVIT) according to the present embodiment is designed for the purpose of finding the optimal rotation and temporal correspondence between two motion signatures. Suppose the two sequences under consideration are represented as matrices whose columns are the stacked values of the acceleration and angular components, $$X = \begin{pmatrix} U_X \\ V_X \end{pmatrix} = \begin{pmatrix} u_X[0] & \cdots & u_X[T_X-1] \\ v_X[0] & \cdots & v_X[T_X-1] \end{pmatrix} \quad (27)$$

$$Y = \begin{pmatrix} U_Y \\ V_Y \end{pmatrix} = \begin{pmatrix} u_Y[0] & \cdots & u_Y[T_Y-1] \\ v_Y[0] & \cdots & v_Y[T_Y-1] \end{pmatrix}$$

The lengths of sequences X and Y are $T_X$ and $T_Y$, respectively.

Figure 8A:
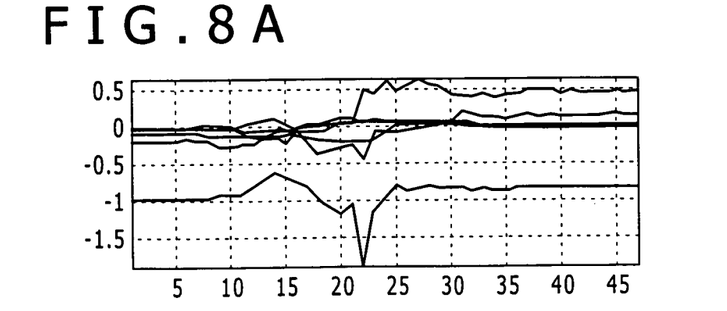
FIG. 8(a) and FIG. 8(b) show example sequences of motion signatures.
Figure 8B:
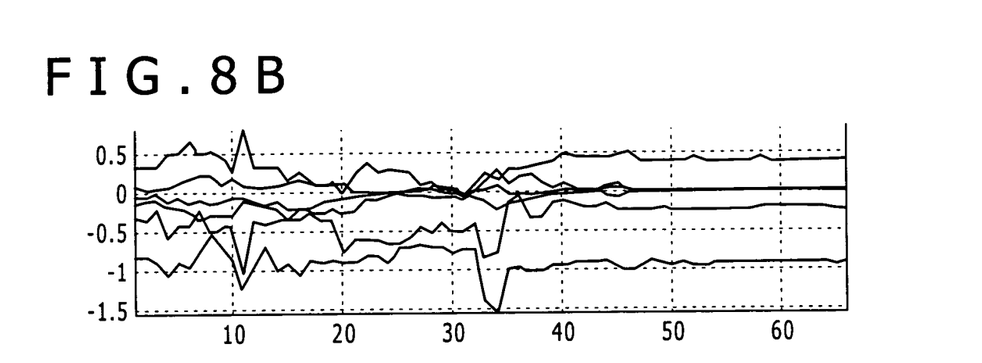

FIG. 8(a) and FIG. 8(b) show examples of two multi-dimensional sequences having possibly different lengths and an arbitrary rotation between them. This particular examples are sequences of motion signatures of a sitting action, but the IMU was oriented differently in each case. Further, the sitting motion in FIG. 8(a) was faster than that of FIG. 8(b).

In order to calculate the similarity between these two sequences to within some arbitrary rotation and some arbitrary time-warping, the problem may be stated as the minimization of the following measure:

$$D_{R,C}(X,Y)=tr((Y-RXC)'(Y-RXC)) \quad (28)$$

over its free parameters which are a rotation matrix, R, and a correspondence matrix, C, where the symbol "'" means a transverse matrix. A correspondence matrix is a special kind of projection matrix that maps the time dimension (columns) of X onto the time dimension (columns) of Y. Suppose we had a function, c(t), that assigns each integer in $\{0, 1, \ldots, T_X-1\}$ to an integer in $\{0, 1, \ldots, T_Y-1\}$. Its correspondence matrix can be constructed as follows:

$$C_{ij} = \begin{cases} 0 & c(i) \neq j \\ 1 & c(i) = j \end{cases} \quad (29)$$

Figure 8C:
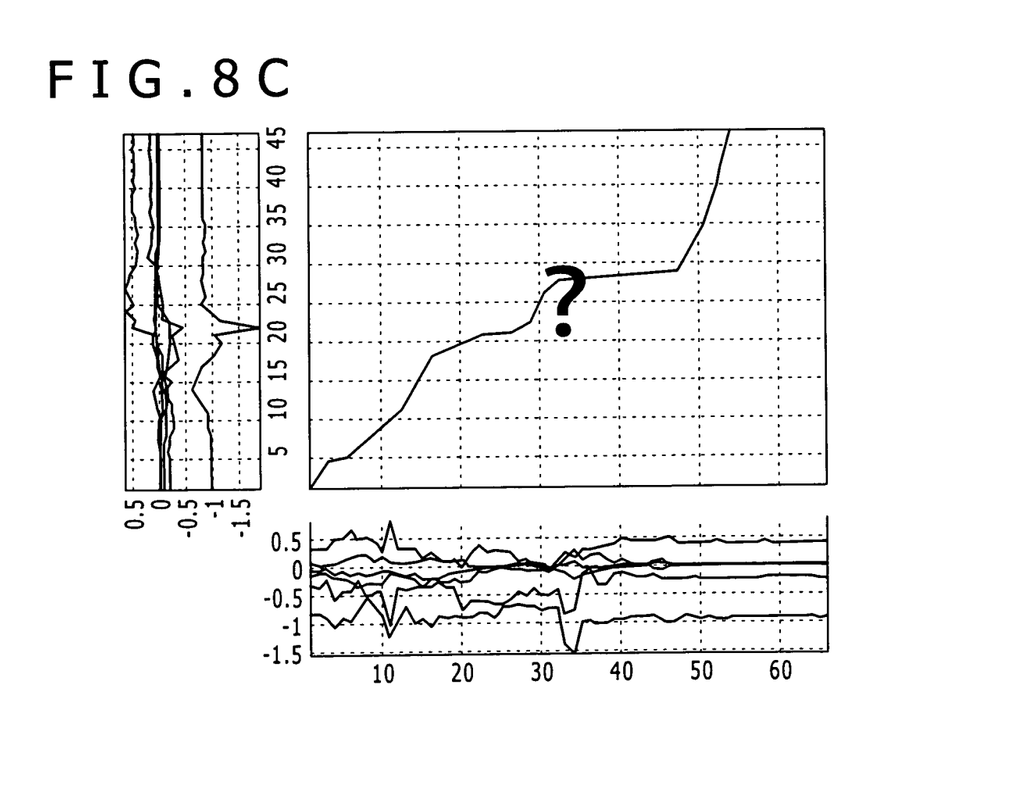
FIG. 8(c) shows matching of two sequences according to an embodiment of the present invention.

While minimizing $D_{R,C}(X, Y)$, it is preferable to constrain C to matrices where the corresponding c(t) is non-decreasing. FIG. 8(c) gives an example of a possible mapping. The optimal C map determines how X should be stretched and compressed (possible deleting some sections and repeating others) to line up with Y. The optimal rotation matrix, R, determines how all the vectors in X should be rotated so that they match the vectors in Y.

The method used in here to minimize the expression (28) is called the coordinate descent method (Non-patent Document 1). It is a simple iterative method that is easily adapted for parallel computation. The idea is to minimize the error function along one single axis in each iteration. This greatly simplifies the minimization problem, as it can be seen, and when it is cycled through each axis, successively minimizing each coordinate, it is known that the Equation will converge to a local minimum. If there were no constraints on R and C then since $D_{R,C}(X,Y)$ is convex this local minimum would also be the global minimum. However, there is constraints in the present embodiment so only localness is guaranteed. In the next Sections, it is described how to minimize the error function over each axis, R and C.

(6.1) Minimizing $D_{R,C}(X, Y)$ over R

There is a simple method for minimizing $D_{R,C}(X, Y)$ over just R. Lets define:

$$R^*(C) \equiv \arg\min_R D_{R,C}(X, Y) \qquad (30)$$

The solution to this minimization problem is well-known as polar decomposition (see Non-patent Document 6 for a detailed derivation) and the solution is:

$$R^*(C) = VU' \qquad (31)$$

Matrices V and U are obtained from the singular value decomposition (SVD) of XCY'=UDV'. It should be noted that the size of XCY' is 6-by-6 so that the cost of the SVD is independent of the length of the sequences.

The inventor of the present application have found that it is beneficial to restrict R so that the same rotation is applied to the gyro and accelerometer components. This means that the structure of R is desirable to be a block diagonal like this:

$$R = \begin{pmatrix} Q & 0 \\ 0 & Q \end{pmatrix} \qquad (32)$$

where Q is 3-by-3 rotation matrix. This constraint can be easily satisfied by calculating Q=VU' but this time V and U are obtained from the SVD of $U_X C U_Y' + V_X C V_Y' = UDV'$.

(6.2) Minimizing $D_{R,C}(X, Y)$ over C

There is also a method for minimizing $D_{R,C}(X, Y)$ over just C using dynamic time warping (DTW). As before, lets define:

$$C^*(R) = \arg\min_C D_{R,C}(X, Y) \qquad (33)$$

Instead of finding C directly as a matrix, the underlying mapping function, c(t) is calculated. Let the vectors of Y sequence represent the states in a Hidden Markov Model (HMM) with left-right topology. Sequence X is matched against the HMM using Viterbi algorithm to provide the optimal path sequence. Scoring of the i-th HMM-state (which represents the i-th vector of Y) on the j-th vector of X is calculated as the squared Euclidean distance:

$$\log P(s_t = i | Y_i, X_j) = -(RX_j - Y_i)'(RX_j - Y_i) \qquad (34)$$

This is equivalent to using unit variance Gaussians centered on the vectors of X to represent the output distributions of each HMM-state, $s_t \in \{0, 1, \ldots, TY-1\}$. The transition probabilities are:

$$\log P(s_t = i | s_{t-1} = j) = \begin{cases} \log \epsilon & j < i \\ -\log 2 & j = i \\ -\dfrac{K(i-j-1)^2}{r_{IMU}} & j > i \end{cases} \qquad (35)$$

where K is an experimentally determined constant (approx. (100/128)Hz in our experiments) and $\epsilon$ is some very small number. Alternatively, the transition probabilities may be determined by using training data.

Using the HMM with parameters specified above as representing Y and an observation sequence as X, the standard Viterbi algorithm is used to find the optimal (maximum likelihood) state path, $\{s_t^*\}$ through the HMM. This state path assigns each vector in X to a vector in Y, according to $c(t) = s_t^*$. The correspondence matrix can then be calculated directly from c(t) as stated above. It should be noted that, in an actual implementation, the matrix product XC is much more efficiently calculated by using c(t) directly to construct XC from X.

(6.3) Determining Initial Conditions

The coordinate descent method, like all descent methods, requires an initial value for at least one of the coordinates. The quality of the local minimum found by coordinate descent is highly sensitive to this initial value. The optimization of $D_{R,C}(X, Y)$ is started with an initial guess for C. The initial value for C is calculated using the same procedure as in Section (6.2) but equation (34) is replaced with, $$\log P(s_t = i | Y_i, X_j) = -(X_j \cdot X_j - Y_i \cdot Y_i)^2 \qquad (36)$$

so that there is no dependence on the rotation matrix, R. This way no rotation matrix is required to find an approximate mapping, c(t), between X and Y.

(6.4) Calculating the Distortion Between X and Y

Below, the procedure, called DISTORTION, is presented for minimizing the error function and thereby calculating the distortion measure between two motion signatures. Let i represent the iteration, and $C^0$ represent the initial guess for C as calculated in Section (6.3) and $\epsilon$ is a stopping criterion used to detect convergence:

---
DISTORTION(X, Y, $C^0$, $\epsilon$) returns $D^{final}$
1.    Initialize $R^0 \leftarrow R^*(C^0)$, $\delta \leftarrow 1$, $i \leftarrow 1$
2.    While $\delta > \epsilon$:
3.       $C^i \leftarrow C^*(R^{i-1})$
4.       $R^i \leftarrow R^*(C^i)$
5.       $D^i \leftarrow D_{R^i, C^i}(X, Y)$
6.       $\delta \leftarrow |D^i - D^{i-1}|$
7.       $i \leftarrow i + 1$
8.    $D^{final} \leftarrow D^i$
---

$R^*(C)$ and $C^*(R)$ are the procedures given in Sections (6.1) and (6.2), respectively. In summary, the DISTORTION procedure calculates a local minimum of $D_{R,C}(X, Y)$ over R and C using the coordinate descent method outlined above. The value returned, $D^{final}$, is a measure of the dissimilarity between X and Y that is invariant to any rotation or time-warping.

(6.5) Device Configuration

Figure 9:
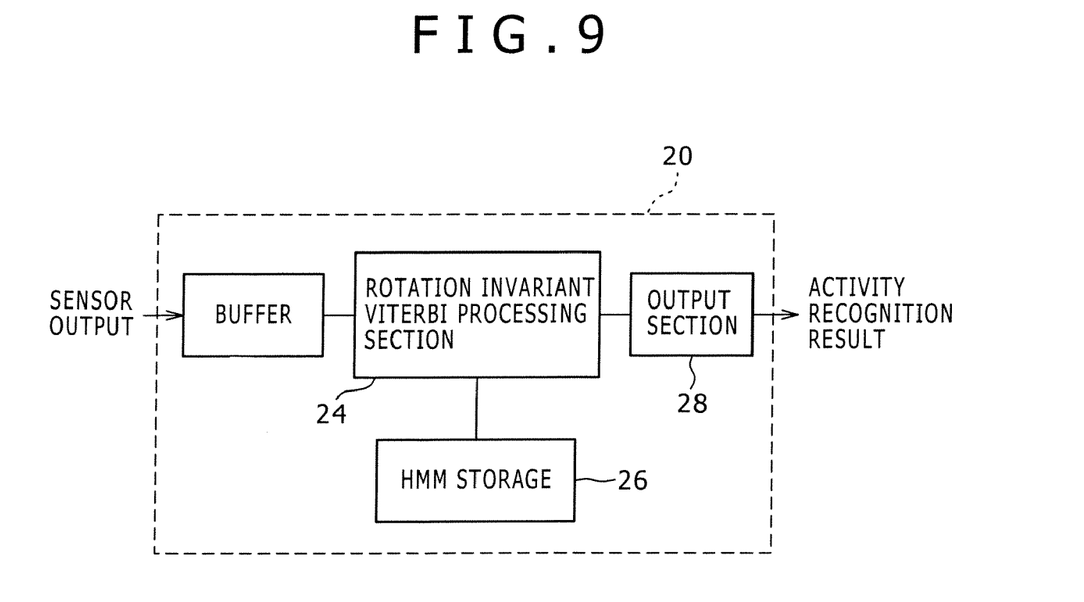
FIG. 9 is a schematic diagram of a computational unit for a method of comparing motion signatures in accordance with an embodiment of the present invention.

The method described in this Section for comparing motion signatures may be realized by the computational unit 20, which may include a CPU and memory for performing processing steps of the method. More specifically, for example, the computational unit 20 may include a buffer, a Rotation Invariant Viterbi (RIVIT) processing section 24, a Hidden Markov Model (HMM) storage 26 and an output section 28 as shown in FIG. 9.

The buffer receives and stores sampled sensor outputs to construct a observation sequence X indicative of motion signature corresponding to a current activity of the subject. The observation sequence X is sent to the RIVIT processing section 24 for finding the optimal rotation and temporal correspondence with a sequence Y, one of sequences represented by the HMM stored in the HMM storage 26. In the RIVIT processing section 24, the optimal rotation may be determined first, and then the optimal temporal correspondence may be determined by matching the sequence X against the HMM using Viterbi to provide the optimal path sequence.

The output section 28 receives the matching result, and outputs as an activity recognition result a signal indicating the current activity of the User. In the present embodiment, it is assumed that the activities may be labeled or classified in advance and mapped against sequences or states of the HMM. The mapping table may be stored in the output section 28 or the sequences or states of the HMM may be labeled.

(7) Method for Determining the Location of the Sensor on the Body

In this Section the method 22 for estimating the location of the IMU with respect to the User's body. Any given movement by the User will generate differing measurements depending on where the IMU is on the User's body, such as in a pocket, being held in the left hand, on a necklace, etc. These differences in measurement of the same action can be used to deduce the location of the IMU. Of course, for this purpose some types of movement are better than others. For example, a motion that only involves the left hand can not be used to distinguish between one situation where the IMU is in the User's left pocket and the situation where the IMU is in the User's right pocket. However, a motion like walking produces unique measurements all over the User's body, except for left-right symmetry.

Figure 5:
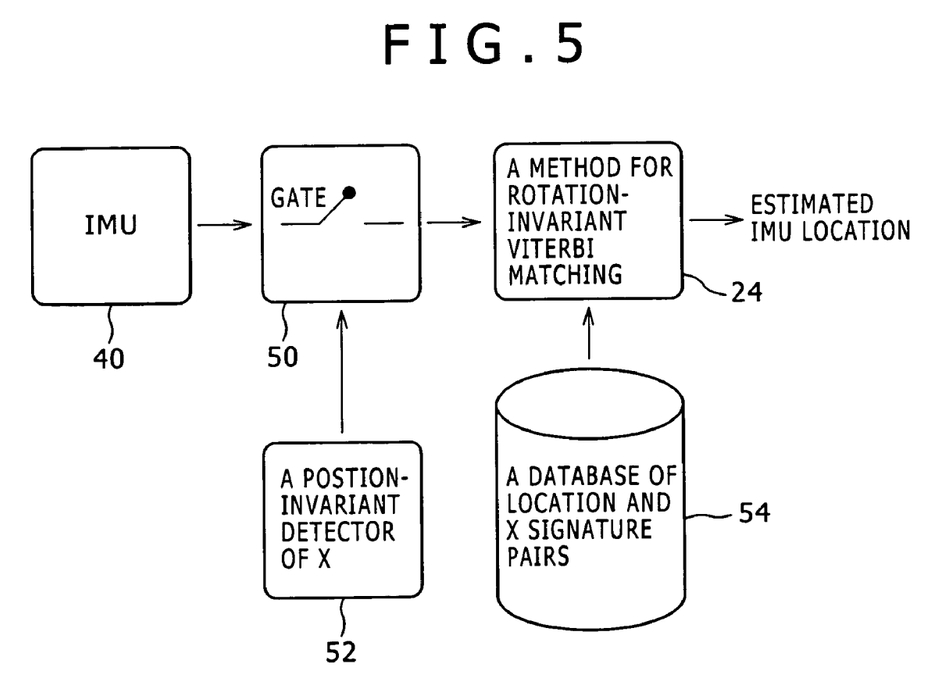
FIG. 5 is an overview of processing pipeline for a method of determining a location of an IMU on a user's body when using a reference motion X.

In this Section, the action or movement used to determine IMU location is referred to as the reference motion. The overall processing pipeline, assuming an arbitrary reference motion X, is depicted in FIG. 5.

A position-invariant detector 52 of the reference motion is used to control GATE 50 to gate the output of the IMU (40), and this way a sequence of test signatures containing the reference motion arrive at the next module 24 For example, if the reference motion is walking then the method 21 for gait frequency measurement (Section (4)can be used as the position-invariant detector.

In the module 24, the test signatures are matched against an exhaustive database 54 of reference motion signatures over locations. The best match indicates the estimated location of the IMU. For generic matching of motion signatures the method in Section (6) may be used. It is also possible to custom-design a matching algorithm for a specific reference motion, especially if it is a periodic motion such as walking.

According to the present embodiment, in its most basic instantiation, the Device is continually outputting what it calculates as the motion that the User has just performed or is performing. What it specifically outputs is determined by the database of motions that are available to the Device for matching. This motion database can be either static or dynamic depending on application needs.

It is also possible to use the Device in a configuration where it is not attached to any human user but rather to a machine or any moving object. Examples of this include vehicles (such as bicycles, cars and boats), factory equipment (such as robotic arms and CNC machinery), plants and animals (such as dogs and cats), cargo (such as a crate of eggs or a drum of volatile liquid).

The classification results can be used directly to drive an application that needs to configure itself based on what the User has been doing or is doing at the moment. These type of applications would be called context-aware and their context-awareness is enabled by, in this case, the Device.

The present invention contains subject matter related to Japanese Patent Application JP 2005-169507 filed in the Japanese Patent Office on Jun. 9, 2005, the entire contents of which being incorporated herein by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An activity recognition apparatus for detecting an activity of a subject, the apparatus comprising:
 a sensor unit including a plurality of linear motion sensors configured to detect linear motions and a plurality of rotational motion sensors configured to detect rotational motions, the linear motions being orthogonal to each other, the rotational motions being orthogonal to each other; and
 a computational unit configured to receive and process signals from the sensors included in the sensor unit so as to detect an activity of the subject,
 wherein the sensor unit is configured to be directly or indirectly supported by the subject with an arbitrary orientation with respect to the subject,
 the computational unit is configured to perform a calculation that uses the signals from the linear motion sensors and rotational motion sensors to determine the activity of the subject independent of the arbitrary orientation of the sensor unit; and
 the computational unit is further configured to detect a rotation of the sensor unit by calculating a first rotation by integrating the signals from the rotational motion sensors, calculating a second rotation by using a gravitation model and the signals from the linear motion sensors, and performing weighted interpolation of the first rotation and the second rotation.

2. The activity recognition apparatus according to claim 1, wherein:
 the plurality of linear motion sensors are three accelerometers for measuring accelerations in three orthogonal axes,
 the plurality of rotational motion sensors are three gyro sensors for measuring angular velocities around the three orthogonal axes, and
 the computational unit is configured to use six outputs from the accelerometers and the gyro sensors to determine a current activity of the subject.

3. The activity recognition apparatus according to claim 1 or 2, the computational unit further comprising:
 a buffer configured to store an observation sequence formed of a plurality set of sensor outputs for a predetermined period of time;
 a storage configured to store a plurality of reference sequences, the reference sequences corresponding to motion signatures of different activities; and
 a matching processor configured to match the observation sequence against the reference sequences to find a best matched reference sequence,
 wherein the matching processor is configured to find an optimal rotation and temporal correspondence between the observation sequence and one of the plurality of reference sequences to obtain the best matched reference sequence.

4. The activity recognition apparatus according to claim 3, wherein the reference sequence includes a plurality of vectors representing states in a Hidden Markov Model, and
the matching between the observation sequence and the reference sequences is performed using a Viterbi algorithm to obtain an optimal state path.

5. The activity recognition apparatus according to claim 1 or 2, wherein
the computational unit is configured to detect a rate of the subject's gait by calculating an autocorrelation of the signals from the linear motion sensors and an autocorrelation of the signals from the rotation motion sensors, and summing these autocorrelations to obtain a summary autocorrelation function, and
the summary autocorrelation function is used to determine the rate of the subject's gait.

6. The activity recognition apparatus according to claim 1 or 2, wherein
a weight for the first rotation is larger when variations in the signals from the rotational motion sensors are smaller, and
a weight for the second rotation is larger when variations in the signals from the linear motion sensors are smaller.

7. The activity recognition apparatus according to claim 1 or 2, further comprising:
a storage configured to store reference motion signatures and corresponding locations for a reference activity, wherein
the computational unit is configured to detect a location of the sensor unit on the subject by determining whether a current activity represented with the signals from the sensors is the reference activity, and, when the current activity is the reference activity, matching a motion signature corresponding to the current activity against the reference motion signatures so as to determine a location of the sensor unit, which corresponds to a best matched reference motion signature.

8. An activity recognition method of determining an activity of a subject, the method comprising:
sampling accelerations in three orthogonal axes and angular velocities around the three orthogonal axes;
determining an activity of the subject using the sampled accelerations and angular velocities; and
detecting a rotation by calculating a first rotation by integrating the sampled angular velocities, calculating a second rotation by using a gravitation model and the sampled accelerations, and performing a weighted interpolation of the first rotation and the second rotation,
wherein the sampled accelerations and angular velocities are detected by sensors integrated into a single unit, which is directly or indirectly supported by the subject with an arbitrary orientation with respect to the subject; and
the determination of activity is performed by using the accelerations and angular velocities to determine the activity independent of the arbitrary orientation of the single unit.

9. A recording medium that stores a program that when executed causes a computer to perform activity recognition by determining an activity of a subject, the program comprising:
receiving data of accelerations in three orthogonal axes and angular velocities around the three orthogonal axes;
determining an activity of the subject using the received data of accelerations and angular velocities; and
detecting a rotation by calculating a first rotation by integrating the received angular velocities, calculating a second rotation by using a gravitation model and the received accelerations, and performing a weighted interpolation of the first rotation and the second rotation,
wherein the accelerations and angular velocities are detected by sensors integrated into a single unit, which is directly or indirectly supported by the subject with an arbitrary orientation with respect to the subject; and
the determination of activity is performed by using the accelerations and angular velocities to determine the activity independent of the arbitrary orientation of the single unit.

* * * * *